(12) United States Patent
Abboud et al.

(10) Patent No.: US 6,562,030 B1
(45) Date of Patent: May 13, 2003

(54) HEATER CONTROL OF CRYOCATHETER TIP TEMPERATURE

(75) Inventors: Marwan Abboud, Pierrefonds (CA); Steven G. Arless, Beaconsfield (CA)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/543,438

(22) Filed: Apr. 5, 2000

Related U.S. Application Data

(60) Provisional application No. 60/127,986, filed on Apr. 6, 1999.

(51) Int. Cl.$^7$ ............................................... A61B 18/18
(52) U.S. Cl. ............................. 606/21; 606/20; 606/24
(58) Field of Search .................................... 606/20–31

(56) References Cited

U.S. PATENT DOCUMENTS

| | | | |
|---|---|---|---|
| 3,298,371 A | * | 1/1967 | Lee ............................... 606/23 |
| 3,910,277 A | * | 10/1975 | Zimmer ......................... 606/23 |
| 3,948,269 A | * | 4/1976 | Zimmer ......................... 606/24 |
| 3,971,383 A | * | 7/1976 | van Gerven .................. 606/23 |
| 4,213,460 A | | 7/1980 | Weiner ..................... 128/303 R |
| 4,487,253 A | | 12/1984 | Malek et al. .............. 165/11 R |
| 4,870,838 A | * | 10/1989 | Zeamer ........................ 62/51.1 |
| 5,807,391 A | * | 9/1998 | Wijkamp ...................... 606/23 |
| 5,818,097 A | * | 10/1998 | Rohlfing et al. ............ 257/468 |
| 6,241,722 B1 | * | 6/2001 | Dobak et al. ................. 606/23 |

FOREIGN PATENT DOCUMENTS

DE    197 24 082 A1    12/1998

* cited by examiner

Primary Examiner—Linda C. M. Dvorak
Assistant Examiner—H M Johnson
(74) Attorney, Agent, or Firm—Christopher & Weisberg, P.A.

(57) ABSTRACT

A cryocatheter includes a catheter body defining a coolant flow path, a catheter tip exposed to the coolant flow path, and a heating element associated with the catheter tip. The heating element can be disposed entirely or partially within the catheter tip. Alternatively, the heating element can be exterior to the catheter tip. The heating element can include an electrically resistive element.

11 Claims, 2 Drawing Sheets

HEATER CONTROL OF CRYOCATHETER TIP TEMPERATURE

CROSS-REFERENCE TO RELATED APPLICATIONS

This application claims priority from U.S. Provisional Patent Application Serial No. 60/127,986, filed Apr. 6, 1999.

STATEMENT REGARDING FEDERALLY SPONSORED RESEARCH

Not applicable.

FIELD OF THE INVENTION

This invention relates to catheters, and more particularly to tip temperature control for cryogenic catheters.

BACKGROUND OF THE INVENTION

A cryocatheter can generally be described as an elongate, slender, flexible body that is capable of delivering extreme cold to provide a medically therapeutic effect. Exemplary cryocatheters are disclosed in U.S. Pat. Nos. 5,899,898 and 5,899,899 to Arless.

Known techniques for creating the extremely low temperatures delivered by a cryocatheter include provision of a cooling chamber where a high pressure gas is allowed to rapidly expand, or where a liquid changes phase to a gas. While both of these techniques can provide extremely cold temperatures (at or above 0° C. to −70° C. or below), it can be very difficult to regulate coolant flow and expansion or phase change with enough precision to ensure that specific temperatures are achieved and maintained. For example, a selected temperature can be therapeutic, but a temperature a few degrees above or below the selected temperature can be either ineffective or injurious.

Additionally, many coolants perform differently under certain conditions. For example, coolant performance can be affected if the coolant absorbs moisture, or if subjected to turbulent flow. Coolant performance is also affected by the particular thermal environment in which it is used and the heat load that it is subjected to.

Prior art cryogenic devices attempt to control temperature, typically at or near the distal tip of the device, by adjusting the injection pressure and volume of coolant in the tip using combinations of pressure regulators and/or pumps. However, for very small diameter catheters (e.g., 3 Fr to 9 Fr), temperature regulation achieved by precise coolant pressure and/or volume control is difficult, especially if one attempts to correct for coolant sensitivity to ambient humidity, room temperature, and temperature variations of a pumping apparatus and a control console. It would therefore be desirable to provide a cryocatheter with improved temperature control features.

SUMMARY OF THE INVENTION

The present invention provides a cryocatheter with improved temperature control features. Whereas prior art cryogenic devices adjust device temperature through a reduction or increase in cooling power by control of coolant flow, the present invention provides an optimized coolant flow and adjusts device temperature with a heating element to reach and maintain a desired temperature.

In an exemplary embodiment, a cryocatheter includes a catheter body defining a coolant flow path, a catheter tip exposed to the coolant flow path, and a heating element associated with the catheter tip. The heating element can be disposed entirely or partially within the catheter tip. Alternatively, the heating element can be exterior to the catheter tip. The heating element can include an electrically resistive element.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
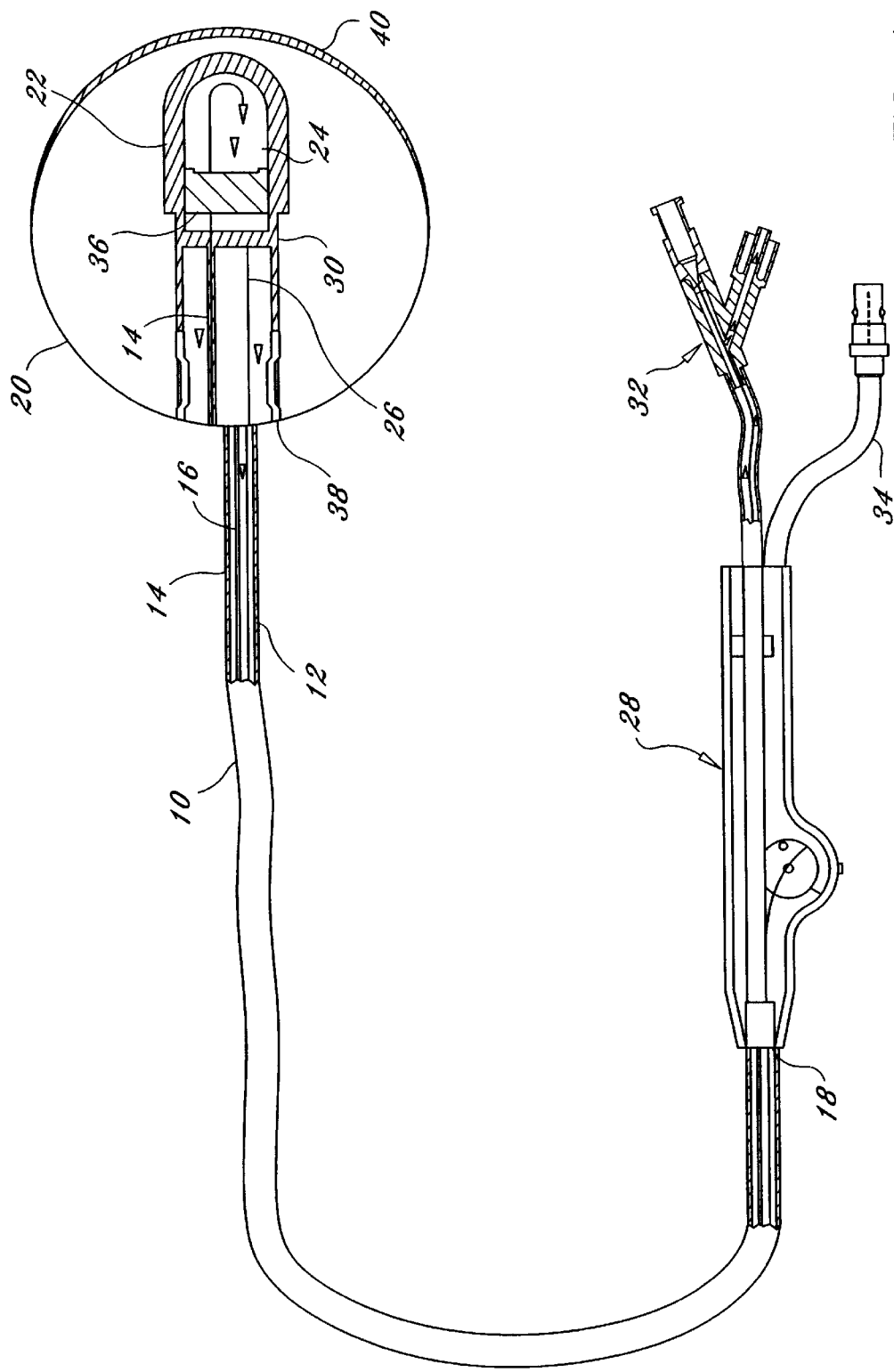
FIG. 1 illustrates a cryocatheter in accordance with the invention with the distal tip enlarged to show detail.

FIG. 1 depicts a cryocatheter in accordance with the invention. The cryocatheter includes a flexible body 10, as is known in the art, that defines or contains two or more lumens. In the illustrated embodiment, the body 10 defines a first lumen 12 within which a tube 14 (defining a second lumen 16) is disposed. The body has a proximal end 18 and a distal end 20. In FIG. 1, the distal end 20 is enlarged to show additional detail.

The distal end 20 includes a tip 22 that seals the body 10 and defines a coolant expansion chamber 24. The tip 22, as well as other portions of the body, can be formed from or include a thermally transmisive material, suitable for cooling or heating tissue or for otherwise performing cryotherapy. In the illustrated embodiment, the second lumen 16, defined by the tube 14, provides a path for coolant (shown by arrows) to flow from a source (not shown) to the cooling chamber 24. Coolant exits the cooling chamber 24 through the first lumen 12, defined by the body 10. Although the cooling chamber 24 is shown at the distal end 20 of the catheter body 10, the cooling chamber can also be configured as a "pass-through" structure, such as a continuous or segmented cylinder, disposed at a point between the proximal and the distal end of the catheter body.

A steering wire 26, in communication with a handle unit 28, is secured to an anchor portion 30. Applying tension to the steering wire 26 causes the catheter body 10 to deflect. The handle unit 28 provides a connection point for a coolant supply and return umbilical 32, as well as a connection point for an electrical/sensor umbilical 34.

A heating element 36 is positioned within the distal end 20 at a location where it can heat the tip 22. A wire 38 connects the heating element 36 to an energy source (not shown). Exemplary heating elements 36 include resistive wires and thin films as are known in the electrical and heating arts. As shown, the heating element 36 is a metal cylinder placed inside the tip 22. In another embodiment, the heating element 36 is a thin film resistance heater which operates at a power of about 10 to 15 Watts. One or more thermocouples 40 are provided to measure temperature of the tip 22.

Figure 2A:
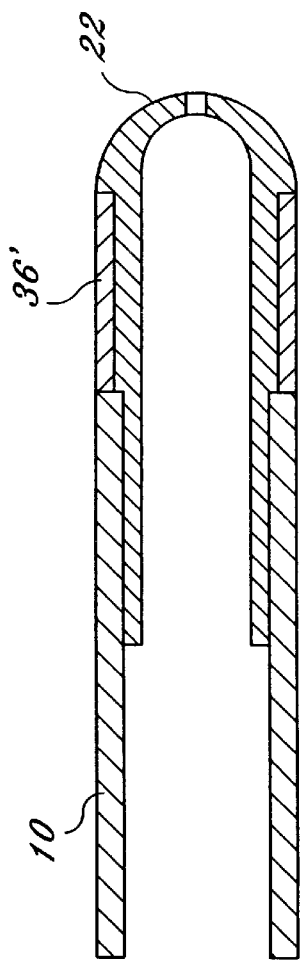
FIGS. 2A and 2B are cross-sectional views of exemplary distal tip embodiments.
Figure 2B:
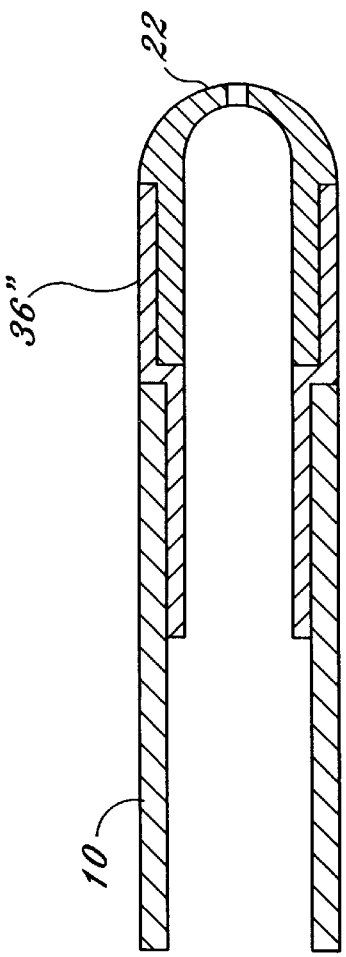

FIGS. 2A and 2B illustrate alternative configurations for the heating element 36. As shown in FIG. 2A, a heating element 36' may be placed on the exterior of the tip 22, whereas the heating element 36 of FIG. 1 is entirely within the tip 22. FIG. 2B illustrates a heating element 36" that includes a first portion within the catheter body 10 and a second portion that is external with respect thereto.

A complete system includes a control console for controlling coolant flow, monitoring tip temperature, and controlling heater activation. Thus, in operation a coolant injection pressure is set at a fixed value which optimizes the cooling efficiency for the selected catheter dimensions and treatment to be performed, as well as to eliminate turbulent flow, cavitation, and bubble formation to provide a selected tip temperature below a selected therapy temperature. For example, the coolant can be injected to provide a temperature of about −60° C. and the heating element 36 can be activated to raise the temperature of the tip 22 to −55° C. In response to thermal changes in the cryocatheter and the tissue being treated, the heating element 36 is energized and de-energized as required to maintain a consistent, selected temperature. In the illustrated embodiments, the heating element 36 is operative to control the catheter tip's temperature between minus 80° C. and approximately plus 37° C.

A variety of modifications and variations of the present invention are possible in light of the above teachings. Specifically, although the heated tip is shown with respect to a slender and flexible catheter, it is also applicable to other embodiments that are thick and rigid. It is therefore understood that, within the scope of the appended claims, the present invention may be practiced otherwise than as specifically described hereinabove. All references cited herein are expressly incorporated by reference in their entirety.

What is claimed is:

1. A cryocatheter comprising:
    a catheter body having a proximal end, a distal end;
    a coolant flow path through the catheter body;
    a cooling chamber exposed to the coolant flow path, said cooling chamber having a selectable cooling temperature; and
    a heating element disposed proximate to the cooling chamber for controlling the selectable cooling temperature of the cooling chamber, the heating element being operated at a power up to 15 Watts,
    wherein at least a portion of the heating element is flush with an inner face of the cooling chamber.

2. The cryocatheter of claim 1, further comprising a thermocouple associated with the cooling chamber.

3. The cryocatheter of claim 1, wherein the heating element includes an electrically resistive element.

4. The cryocatheter of claim 1, wherein the heating element includes a thin film resistance heater.

5. The cryocatheter of claim 1, wherein the cooling chamber seals the distal end of the catheter body and defines a coolant expansion chamber, and wherein the heating element is disposed within the coolant expansion chamber.

6. The cryocatheter of claim 1, further comprising coolant operative to cool an exterior portion of the cooling chamber to approximately −80° C., and wherein the heating element is operative to control the temperature of the exterior portion of the cooling chamber to a temperature between −80° C. and approximately +37° C.

7. A cryocatheter comprising:
    a catheter body having a proximal end, a distal end;
    a coolant flow path through the catheter body;
    a cooling chamber exposed to the coolant flow path, said cooling chamber having a selectable cooling temperature; and
    a heating element disposed proximate to the cooling chamber for controlling the selectable cooling temperature of the cooling chamber, the heating element being operated at a power up to 15 Watts,
    wherein the heating element is disposed on an outer surface of the cooling chamber.

8. A cryocatheter comprising:
    a catheter body having a proximal end, a distal end;
    a coolant flow path through the catheter body;
    a cooling chamber exposed to the coolant flow path, said cooling chamber having a selectable cooling temperature; and
    a heating element disposed proximate to the cooling chamber for controlling the selectable cooling temperature of the cooling chamber, the heating element being operated at a power up to 15 Watts,
    wherein a first portion of the heating element is disposed on an outer surface of the cooling chamber and a second portion of the heating element is disposed within the coolant flow path.

9. A cryocatheter comprising:
    a catheter body having a proximal end, a distal end;
    a coolant flow path through the catheter body;
    a cooling chamber exposed to the coolant flow path, said cooling chamber having a selectable cooling temperature; and
    a heating element disposed proximate to the cooling chamber for controlling the selectable cooling temperature of the cooling chamber, the heating element being operated at a power up to 15 Watts,
    wherein at least a portion of the heating element is flush with the catheter body.

10. A cryocatheter comprising:
    a catheter body having a proximal end, a distal end;
    a coolant flow path through the catheter body;
    a cooling chamber exposed to the coolant flow path, said cooling chamber having a selectable cooling temperature; and
    a heating element disposed proximate to the cooling chamber for controlling the selectable cooling temperature of the cooling chamber, the heating element being operated at a power up to 15 Watts,
    wherein at least a portion of the heating element is flush with an outer face of the cooling chamber.

11. A method of controlling cryocatheter tip temperature comprising the steps of:
    providing a cryocatheter having
        a catheter body having a proximal end, a distal end, and a coolant flow path from the proximal end to the distal end,
        a catheter tip exposed to the coolant flow path, and
        a heating element associated with the catheter tip, the heating element being operated at a power up to 15 Watts,
    circulating coolant through the coolant flow path at a fixed rate; and
    energizing the heating element as required to maintain a selected temperature for the catheter tip.

* * * * *

UNITED STATES PATENT AND TRADEMARK OFFICE
CERTIFICATE OF CORRECTION

PATENT NO. : 6,562,030 B1
DATED : May 13, 2003
INVENTOR(S) : Marwan Abboud et al.

It is certified that error appears in the above-identified patent and that said Letters Patent is hereby corrected as shown below:

<u>Column 13,</u>
Line 19, insert -- In addition to providing precise temperature control, the heating element 36 allows the selected temperature to be changed more rapidly that would be possible by reducing coolant flow alone. Additionally, the control console can be more simple than a console of the prior art because relatively complicated fluid control regulators are not required. --

Signed and Sealed this

Second Day of December, 2003

JAMES E. ROGAN
*Director of the United States Patent and Trademark Office*